US012704657B2

(12) United States Patent
Khalifa et al.

(10) Patent No.: US 12,704,657 B2
(45) Date of Patent: Aug. 11, 2026

(54) METHOD FOR ESTABLISHING A COMPUTER-AIDED TOMOGRAPHY INDEX FOR THE IMPROVEMENT OF PETROPHYSICAL PROPERTIES

(71) Applicant: SAUDI ARABIAN OIL COMPANY, Dhahran (SA)

(72) Inventors: Aqeel M. Khalifa, Dammam (SA); Paul J. Tarabbia, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 817 days.

(21) Appl. No.: 18/050,879

(22) Filed: Oct. 28, 2022

(65) Prior Publication Data

US 2024/0142662 A1 May 2, 2024

(51) Int. Cl.

| | |
|---|---|
| ***G01V 11/00*** | (2006.01) |
| ***E21B 47/002*** | (2012.01) |
| ***G01N 33/24*** | (2006.01) |
| ***G01N 33/28*** | (2006.01) |
| ***G06F 30/20*** | (2020.01) |

(52) U.S. Cl.

CPC ............ *G01V 11/00* (2013.01); *E21B 47/002* (2020.05); *G01N 33/241* (2013.01); *G01N 33/2823* (2013.01); *G06F 30/20* (2020.01); *E21B 2200/20* (2020.05)

(58) Field of Classification Search

CPC ... G01V 11/00; E21B 47/002; E21B 2200/20; E21B 49/02; G01N 33/241; G01N 33/2823; G06F 30/20

See application file for complete search history.

(56) References Cited

U.S. PATENT DOCUMENTS

| | | | | |
|---|---|---|---|---|
| 8,101,907 | B2 | 1/2012 | Jacobi et al. | |
| 9,507,047 | B1 | 11/2016 | Dvorkin et al. | |
| 10,502,863 | B2 | 12/2019 | Mosse et al. | |
| 10,591,630 | B2 * | 3/2020 | Berheide | G01V 5/101 |
| 10,983,246 | B2 * | 4/2021 | Mosse | G01V 3/32 |
| 2009/0157367 | A1 | 6/2009 | Meyer et al. | |
| 2019/0195061 | A1 * | 6/2019 | Ramsay | G01V 8/02 |
| 2021/0132026 | A1 * | 5/2021 | Nie | G01N 33/24 |
| 2021/0231827 | A1 | 7/2021 | Grau et al. | |

(Continued)

FOREIGN PATENT DOCUMENTS

WO WO-2021086388 A1 * 5/2021 ............ G06F 30/20

OTHER PUBLICATIONS

WO-2021086388-A1_translated (Year: 2021).*

(Continued)

*Primary Examiner* — Catherine T. Rastovski
*Assistant Examiner* — Michael J Singletary
(74) *Attorney, Agent, or Firm* — Vorys, Sater, Seymour and Pease LLP

(57) ABSTRACT method for characterizing an oil well may include obtaining measurements of petrophysical properties relating to the oil/gas or water well, obtaining a computer-aided tomography index measured on a core sample relating to the well that is matched to geochemical concentration from geochemical logs or rock-analysis, correcting the measurements of petrophysical properties as a function of the computer-aided tomography index, and developing a model of a subterranean formation using the measurements that were corrected.

13 Claims, 6 Drawing Sheets

(56) References Cited

U.S. PATENT DOCUMENTS

| | | | | |
|---|---|---|---|---|
| 2022/0351037 | A1* | 11/2022 | Li | G01N 21/3563 |
| 2023/0186564 | A1* | 6/2023 | AlBahrani | G06T 17/05<br>345/423 |
| 2023/0304391 | A1* | 9/2023 | Sheng | E21B 25/00 |
| 2024/0011392 | A1* | 1/2024 | AlBahrani | G06F 30/23 |

OTHER PUBLICATIONS

Defining Logging (Anderson, Mark, Sep. 9, 2015, https://www.slb.com/resource-library/oilfield-review/defining-series/defining-logging) (Year: 2015).*
Defining Logging (Year: 2015).*

* cited by examiner

METHOD FOR ESTABLISHING A COMPUTER-AIDED TOMOGRAPHY INDEX FOR THE IMPROVEMENT OF PETROPHYSICAL PROPERTIES

FIELD OF THE DISCLOSURE

The present disclosure relates generally to the determination of petrophysical properties for wellbores and, more particularly, to the improvement of this determination through the use of a computer-aided tomography index that is tied to Rock Inorganic Geochemistry.

BACKGROUND OF THE DISCLOSURE

In the oil and gas industry, petrophysical properties are commonly used to determine the quantity and flow potential of an oil well. The petrophysical properties commonly studied may include lithology, permeability, water saturation, formation density, and porosity. Measurements of these properties may be obtained via the analysis of drilled core samples, wireline or logging while drilling (LWD) logs that include geochemical log measurements, or through seismic processing. Petrophysical properties may be used in the development of static and dynamic reservoir models, which can estimate the rate of extraction from the well, the amount of hydrocarbons stored within the well, as well as the simulated fluid flow within the pores of the rock. However, in order to produce accurate estimates, the measurements of the petrophysical properties must be accurate and free of any errors due to assumptions.

One factor which may cause deviation between the true petrophysical properties and the measured petrophysical properties is the determination of grain density within a rock sample. As the grain density calculation fails to account for the presence of additional solid material within the sample, the use of this petrophysical property for any further analysis or modelling of complex samples can lead to expounding errors. Further, the pore volume of subsurface rock units can be altered through geological processes such as burial and diagenetic cementation. The cement phases in these units may vary significantly and affect the determination of accurate petrophysical properties within the well, such as the storage capacity and permeability. These variations may lead to the inaccurate determination of reservoir porosity, which could lead to the sub-optimal reservoir characterization and well design. As such, a method for handling the inconsistencies present in the sampling methods and for the correction of grain density calculations is necessary for the accurate modelling of reservoirs.

SUMMARY OF THE DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

According to an embodiment consistent with the present disclosure, a method for characterizing an oil well may include obtaining measurements of petrophysical properties relating to the oil well, obtaining a computer-aided tomography index measured on a core sample relating to the well, correcting the measurements of petrophysical properties as a function of the computer-aided tomography index, and developing a model of a subterranean formation using the measurements that were corrected.

In another embodiment, a system may include a processor of an electronic device and a non-transitory computer-readable medium. The non-transitory computer-readable medium may store machine-readable instructions, which, when executed by the processor, cause the electronic device to receive a computer-aided tomography scan of a core sample from a subterranean formation, generate a computer-aided tomography index of the core sample, match the cement geochemical element value using geochemical logs, calculate corrected petrophysical properties for the subterranean formation and an associated reservoir, and perform reservoir management utilizing the corrected petrophysical properties.

Any combinations of the various embodiments and implementations disclosed herein can be used in a further embodiment, consistent with the disclosure. These and other aspects and features can be appreciated from the following description of certain embodiments presented herein in accordance with the disclosure and the accompanying drawings and claims.

DETAILED DESCRIPTION

Figure 1:
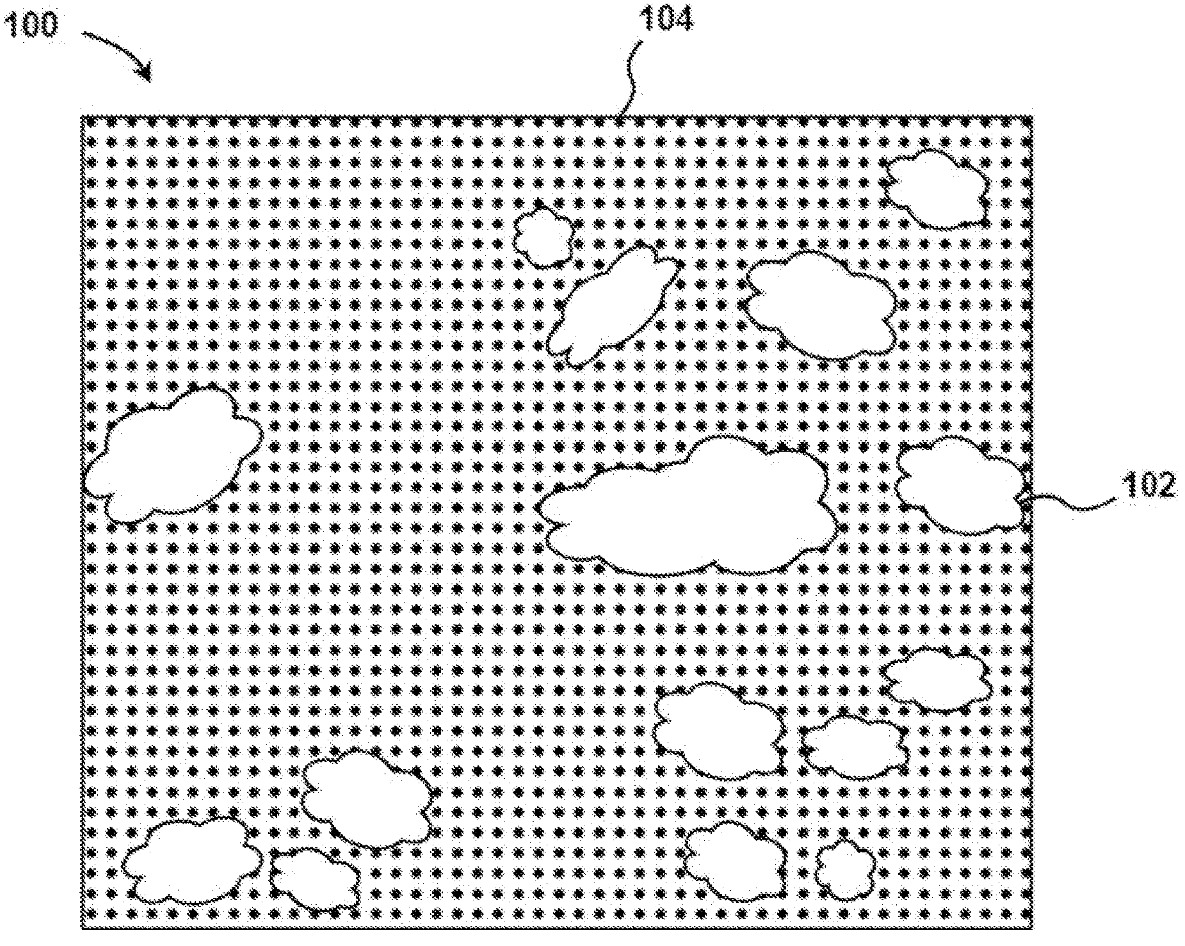
FIG. 1 is an example rock sample with a cement phase distributed within the rock matrix.

Embodiments of the present disclosure will now be described in detail with reference to the accompanying Figures. Like elements in the various figures may be denoted by like reference numerals for consistency. Further, in the following detailed description of embodiments of the present disclosure, numerous specific details are set forth in order to provide a more thorough understanding of the claimed subject matter. However, it will be apparent to one of ordinary skill in the art that the embodiments disclosed herein may be practiced without these specific details. In other instances, well-known features have not been described in detail to avoid unnecessarily complicating the description. Additionally, it will be apparent to one of ordinary skill in the art that the scale of the elements presented in the accompanying Figures may vary without departing from the scope of the present disclosure.

Embodiments in accordance with the present disclosure generally relate to the determination of petrophysical properties for wellbores and, more particularly, to the improvement of this determination through the use of a computer-aided tomography index that is matched to geochemical concentration from geochemical logs. This approach may integrate the outputs of a defined computer-aided tomography (CT) index, measured on a core sample, with the elemental concentration values of the rock, obtained via borehole geochemical logging tools. The CT index may then be used to correct for the grain density calculations and improve the computed petrophysical properties. Further, with the determination of the CT index as well as the correlation to the elemental concentration values of the rock, this method may enable the relationship to be extended to wellbores where the core samples are unavailable and geochemical logs are present.

FIG. 1 is an example rock sample 100 with a cement phase distribution 102 within a rock matrix 104. In the illustrated embodiment, the cement phase distribution 102 comprises a variety of patchy cements (may include anhydrite, barite, siderite, pyrites, sulphides, etc.), while the rock matrix 104 comprises either a sandstone or carbonate. As previously stated, in the current state of the art the rock sample 100 would be assessed with a grain density determination. In the grain density determination, the rock sample 100 would be assumed to be completely formed of the sandstone or carbonate of the rock matrix 104 while omitting the presence of the patchy cement phase distribution 102. In this way, it may be seen that variations may exists between the true grain density and the determined grain density, which may propagate to further calculations and determinations relevant to the subterranean formation. These variations may lead to the inaccurate determination of reservoir porosity, which could lead to the sub-optimal reservoir characterization and well design. As such, for samples such as the rock sample 100, a method of correction is needed to ensure proper assessment of rock petrophysical properties.

Figure 2:
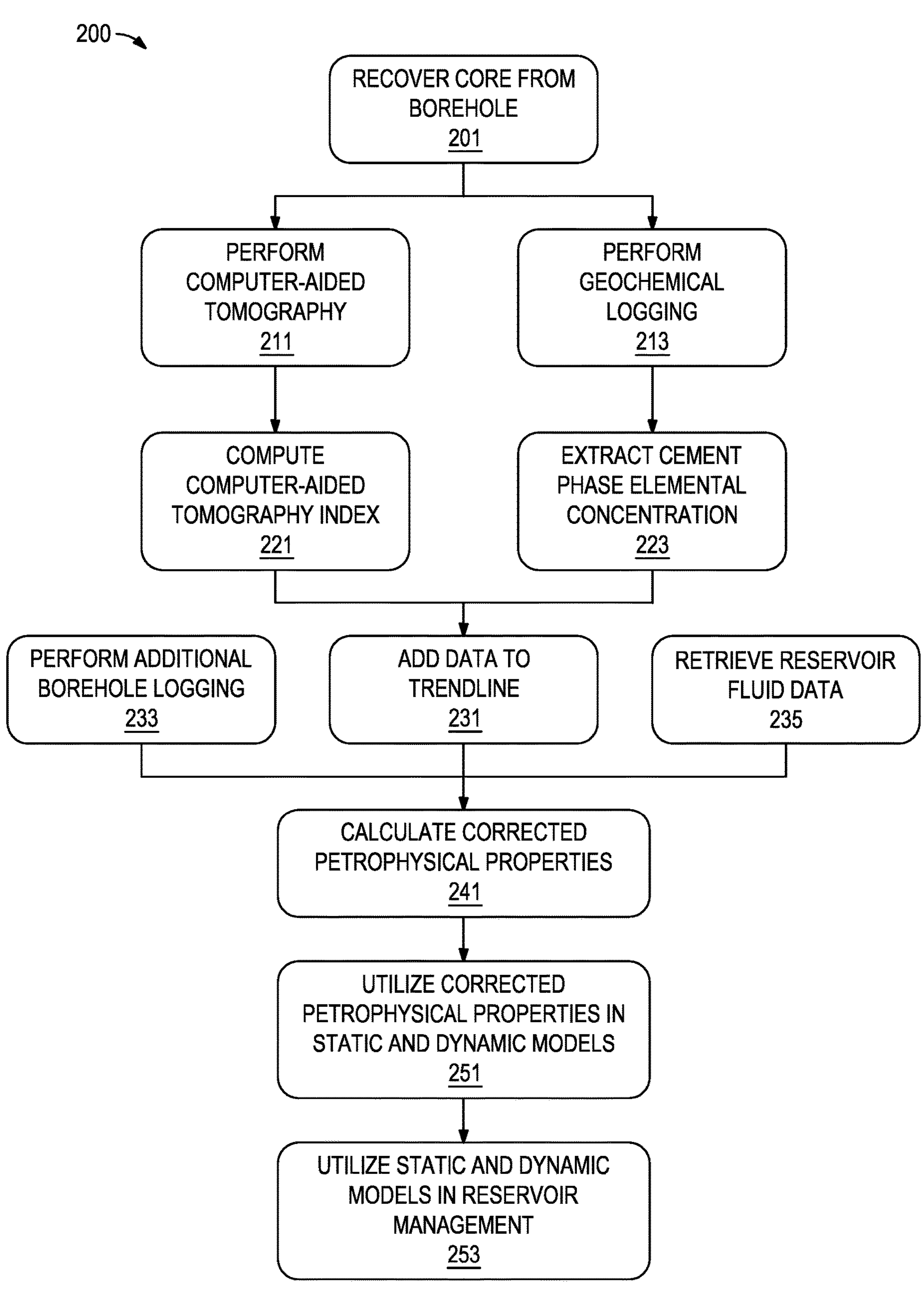
FIG. 2 is a flowchart of an example method for the correction of petrophysical properties using a computer-aided tomography index as well as elemental concentration values.

FIG. 2 is a flowchart of an example method 200 for the correction of petrophysical properties using a computer-aided tomography index as well as elemental concentration values. The method 200 may begin at 201 with the recovery of a core sample from a borehole. The recovered core sample may then be utilized at 211 with the performance of a computer-aided tomography scan on the core sample. The computer-aided tomography scan performed at 211 allows for a clear understanding of the interior structure of the core sample, as well as the distribution of additional mineral components within complex core samples. Additionally, at 213, a geochemical logging may be performed within the drilled wellbore. The geochemical logging performed at 213 may be done using an elemental capture spectroscopy device, a pulsed neutron spectroscopy device, or using any other geochemical logging procedure which provides a log of elemental concentrations within the rock surrounding the wellbore.

With the analysis of the core sample at 211 and of the borehole at 213, several calculations may be made as a result. At 221, the computer-aided tomography scan performed at 211 enables the derivation of an index which may denote a value based upon the porosity of the sample, the complexity or ratio of the diagenetic phases with high density material present within the core sample, a representative grain density value, and/or a density average value per unit of rock which is proportionally related to the density of the rock sample. This index can be computed at a dynamic scale ranging from 500 microns up to several feet. Similarly, at 223, the geochemical logging performed at 213 enables the extraction of the elemental concentration within the cement phase of the rock surrounding the borehole. At 223, the extraction of the elemental concentration may be performed with a mineralogy or elemental analysis, with the mineralogy or elemental analysis including, but not limited to, X-ray folourecense, inductively coupled plasma mass spectrometry, X-ray diffraction, and scanning electron microscopy. This elemental concentration extracted at 223 may correspond to the higher density material found in the computer-aided tomography scan at 211 and incorporated into the computer-aided tomography index at 221. As such, the computer-aided tomography index derived at 221 and the elemental concentration extracted at 223 may be compiled at 231. With the compilation of the data obtained from both the computer-aided tomography scan and the geochemical logging at 231, the future analysis of existing wells may be performed as described further herein. The computer-aided tomography index and the elemental concentrations may be correlated in a trendline at 231, such that a more reliable prediction may be made in future tests with only the requirement for either the computer-aided tomography index or the elemental concentrations. The trendline at 231 may comprise a linear, logarithmic, polynomial, power, or moving average trend, such that the correlation may be made between the computer-aided tomography index and the elemental concentrations. In some embodiments, the trendline's R 2 value may be evaluated against a certain significance level and sample size. For example, a significance level of 0.05 with a sample size of 10 would mean that an R 2 value of 0.63 or greater is considered significant, while for the same significance level, a sample size of 20 would mean that an R 2 value of 0.45 or greater is considered significant.

After the compilation of the data, and the possible generation of the trendline, at 231, additional tests may be performed on the subterranean formation and the reservoir fluid of the associated reservoir. At 233, further logging may be performed within the borehole to obtain data which may further aid in the determination of the petrophysical properties. The further logging performed at 233 may be done through the use of mechanical, acoustical, fluid, nuclear, electrical or imaging devices. In addition, testing may be performed on extracted reservoir fluid at 235 which may produce fluid properties and phase behavior which may enable further understanding of the rock and fluid system surrounding the borehole and the subterranean formation. With the data sourced from 231, 233, and 235, a corrected calculation of the petrophysical properties may be obtained at 241.

The corrected petrophysical properties determined at 241 may enable better production well system design, more accurate predictions for well quality and output, and may further improve 3D geological models at 251. The corrected petrophysical properties may enable enhanced modelling for both static and dynamic models at 251 to better characterize and predict production from the well of interest. The enhanced static and dynamic models may be directly utilized in reservoir management at 253, such that the reservoir or well of interest may be properly utilized. The reservoir management which is affected at 253 may include, but is not limited to, adjustment of estimated reservoir volume and/or projected flowrate, optimization of wellbore design, alteration of the depletion plan, and the preemptive correction of reservoir issues. Those skilled in the art will appreciate that the corrected petrophysical properties may be utilized in additional functions not expressly disclosed herein without departing from the scope of the present disclosure.

Figure 3:
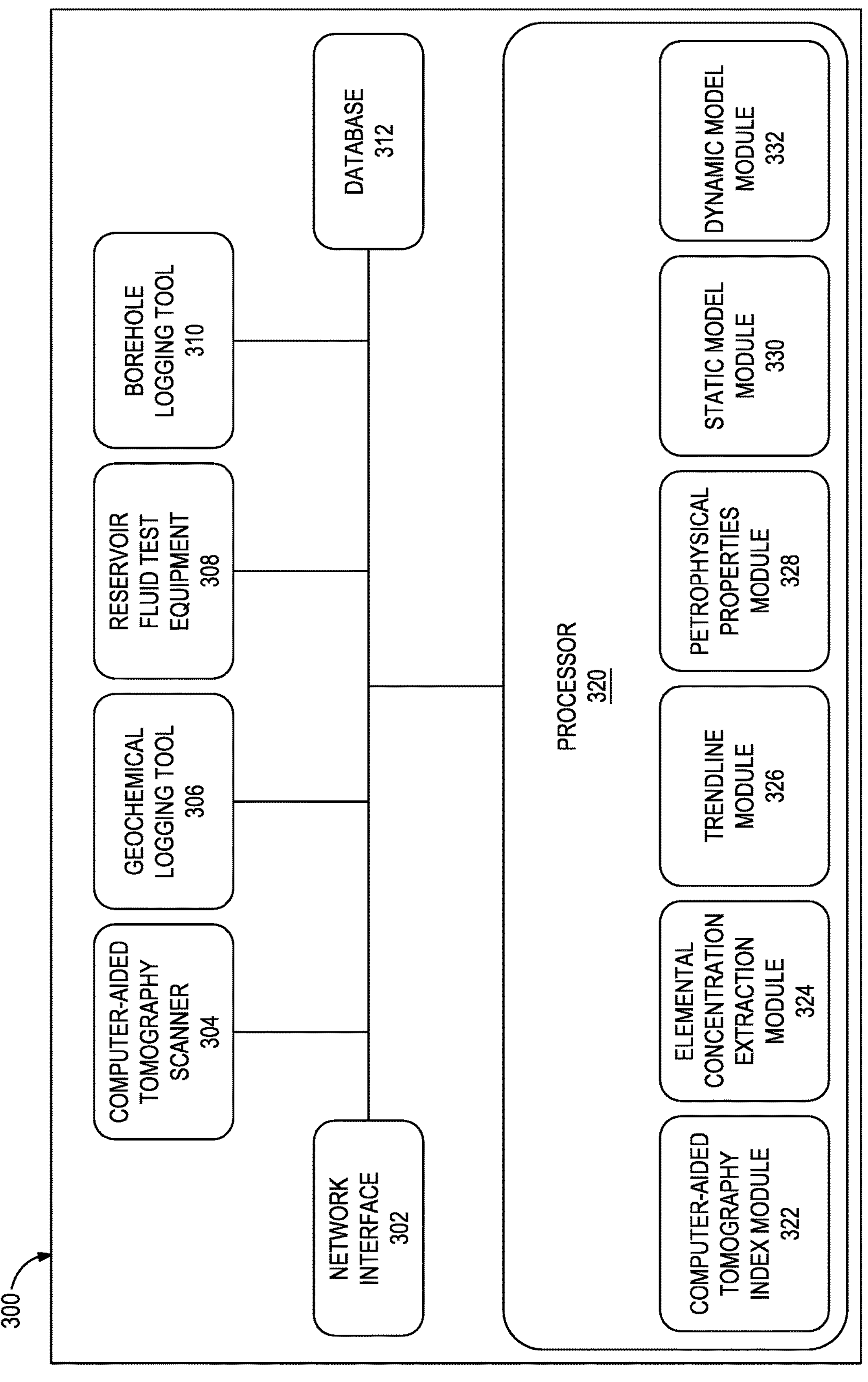
FIG. 3 is a block diagram of an example system for the correction of petrophysical properties.

FIG. 3 is a block diagram of an example system 300 for the correction of petrophysical properties. In some embodiments, the system 300 may represent a single system in one location, with physical connections passing information between the components of the system 300. However, in some embodiments, the system 300 may represent a series of separate devices or apparatuses which are present in multiple locations, such that information is passed between the components over a network interface 302. As such, the network interface 302 may further represent a single unit or multiple units linked to each component such that information may be relayed between components.

As a part of the system 300, a computer-aided tomography scanner 304 may be included, such that core samples may be scanned to be used in the determination of a computer-aided tomography index. Similarly, a geochemical logging tool 306 may be included as a part of the system 300, such that the obtaining and processing of the geochemical logs may be performed within a unified system 300. The further testing of the reservoir fluid and the borehole may be performed by reservoir fluid test equipment 308 and at least one borehole logging tool 310, such that all physical testing of the wellbore, the core sample, and the reservoir fluid may be handled by the system 300.

In the illustrated embodiment, the system 300 includes a database 312 and a processor 320. The database 312 may comprise information from the test equipment previously described, as well as historical data for the previously described measurements. This data, as well as any new information sourced from the previously described test equipment, may be used by the processor 320 and its corresponding modules. The processor 320 may include a computer-aided tomography index module 322, which is utilized in the determination of a computer-aided tomography index utilizing the computer-aided tomography scan sourced from the computer-aided tomography scanner 304 or the database 312. Similarly, the processor 320 may include an elemental concentration extraction module 324 which may analyze the information from the geochemical logging tool 306 or the database 312 to extract the elemental concentration of the minerals or other components within the sample.

The processor 320 may further include a trendline module 326 which may generate a trendline as previously described to correlate the computer-aided tomography index with the elemental concentration extracted in the elemental concentration extraction module 324. The trendline module 326 may further incorporate historical data sourced from the database 312 in the correlation of the previously described properties. The processor 320 may include a petrophysical properties module 328, which utilizes the trendline and correlations developed in the trendline module 326, or stored on the database 312, in order to correct the petrophysical properties going forward. The corrected petrophysical properties may enable better production well system design, more accurate predictions for well quality and output, and may further improve 3D geological models within the static model module 330 and the dynamic model module 332. The corrected petrophysical properties may enable enhanced modelling for both static and dynamic models to better characterize and predict production from the well of interest. The enhanced static and dynamic models generated by the static model module 330 and the dynamic module 332 may be directly utilized in reservoir management, such that the reservoir or well of interest may be properly utilized. The reservoir management which is affected by these models may include, but is not limited to, adjustment of estimated reservoir volume and/or projected flowrate, optimization of wellbore design, alteration of the depletion plan, and the preemptive correction of reservoir issues. Those skilled in the art will appreciate that the corrected petrophysical properties may be utilized in additional functions not expressly disclosed herein without departing from the scope of the present disclosure.

Figure 4:
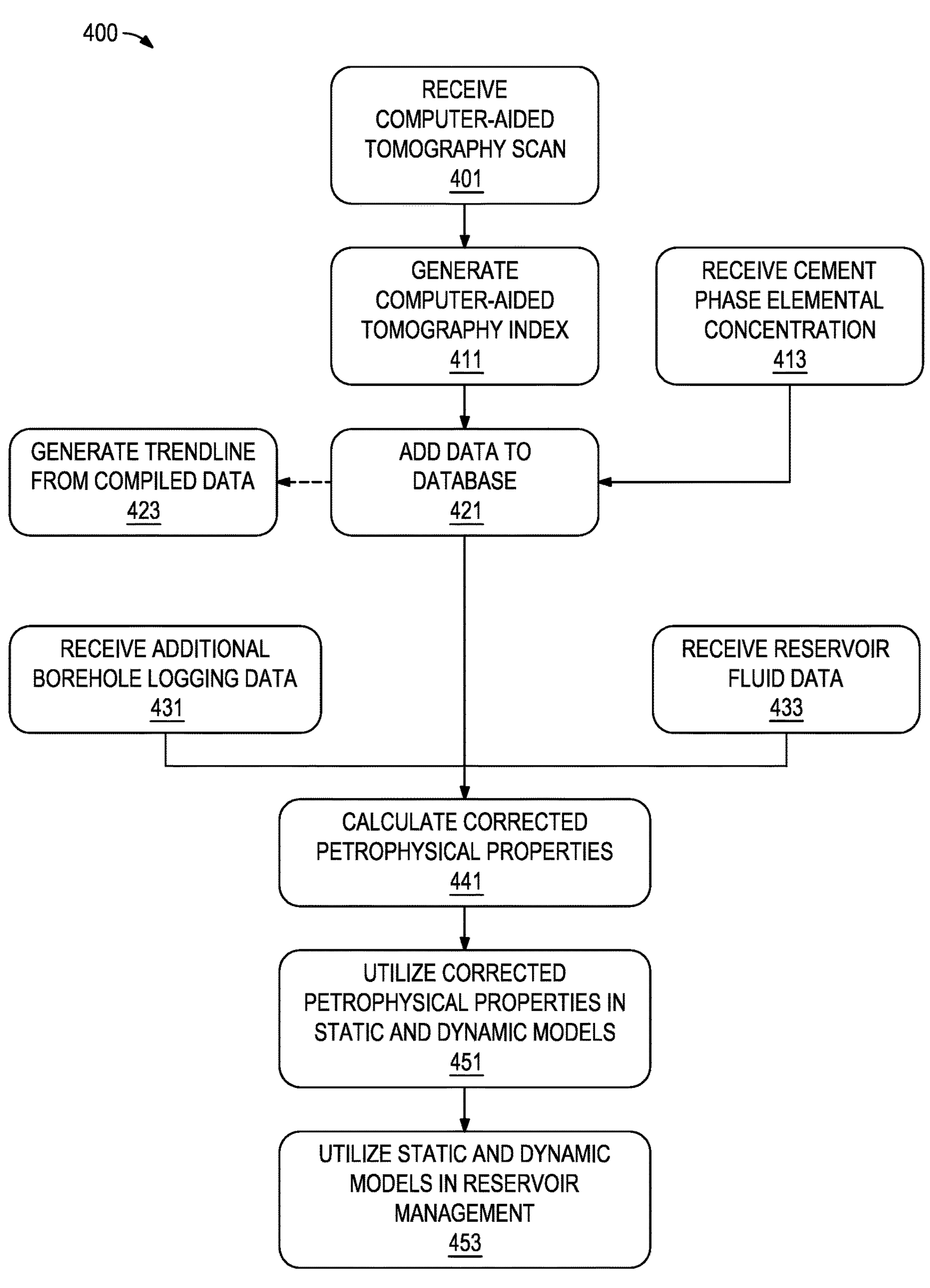
FIG. 4 is a flowchart of an example computer-implemented method which receives wellbore logging data inputs to modify the static and dynamic models for the management of a reservoir.

FIG. 4 is a flowchart of an example computer-implemented method 400 which may receive wellbore logging data inputs to modify the static and dynamic models for the management of a reservoir. The computer-implemented method 400 may begin at 401, in which the computer or electronic device receives a computer-aided tomography scan of a core sample from a wellbore (e.g., from the computer-aided tomography scanner 304 of FIG. 3). It should be noted that the computer which aids in the computer-aided tomography scan may be the same computer which implements the computer-implemented method 400, such that the scan may not be received from an external source but from an internal process.

Upon receiving the scan at 401, the method 400 may continue at 411 with the generation of the computer-aided tomography index. In addition, the method 400 may comprise receiving a cement phase elemental concentration as an input at 413. The cement phase elemental concentration may be received from geochemical logging tools (e.g., the geochemical logging tool 306 of FIG. 3), which may include natural gamma ray spectroscopy, elemental capture spectroscopy, pulsed neutron spectroscopy, aluminum activation, any other geochemical logging method which provides a log of elemental concentrations within the rock surrounding the wellbore, or calculated through a processor module (e.g., the elemental concentration extraction module 324 of FIG. 3). With both the cement phase elemental concentration received at 413, and the computer-aided tomography index generated at 411, the data may be compiled and added to a database (e.g., the database 312 of FIG. 3) at 421. Additionally, if the amount of data within the database reaches a predefined quantity, the method 400 may further include generating a trendline from the compiled data at 423 through the use of a processor module (e.g., the trendline module 326 of FIG. 3). It should be noted that once the trendline is generated at 423, the trendline may be updated at 423 with each successive performance of the method 400, as new data is added at 421.

After the compilation of the data at 421, the method may involve the receiving of additional borehole logging data at 431, and receiving reservoir fluid data at 433 from additional data acquisition (e.g., the reservoir fluid test equipment 308 and the borehole logging tool 310 of FIG. 3). The additional borehole logging performed at 431 may be done through the use of mechanical, acoustical, fluid sampling, nuclear, electrical or imaging devices. In addition, the testing performed on extracted reservoir fluid at 433 may produce fluid properties and phase behavior which may enable further understanding of the rock and fluid system surrounding the borehole. With the three sources of data discussed herein, the method 400 may advance to 441, in which the data may be integrated in order to calculate corrected petrophysical properties for the wellbore and reservoir with a processor module (e.g., the petrophysical properties module 328 of FIG. 3).

The corrected petrophysical properties determined at 441 may enable better production well system design, more accurate predictions for well quality and output, and may further improve 3D geological models at 451. The corrected petrophysical properties may enable enhanced modelling for both static and dynamic models at 451 to better characterize and predict production from the well of interest. The enhanced static and dynamic models may be directly utilized in reservoir management at 453, such that the reservoir or well of interest may be properly utilized. The reservoir management which is affected at 453 may include, but is not limited to, adjustment of estimated reservoir volume and/or projected flowrate, optimization of wellbore design, alteration of the depletion plan, and the preemptive correction of reservoir issues. Those skilled in the art will appreciate that the corrected petrophysical properties may be utilized in additional functions not expressly disclosed herein without departing from the scope of the present disclosure.

Figure 5:
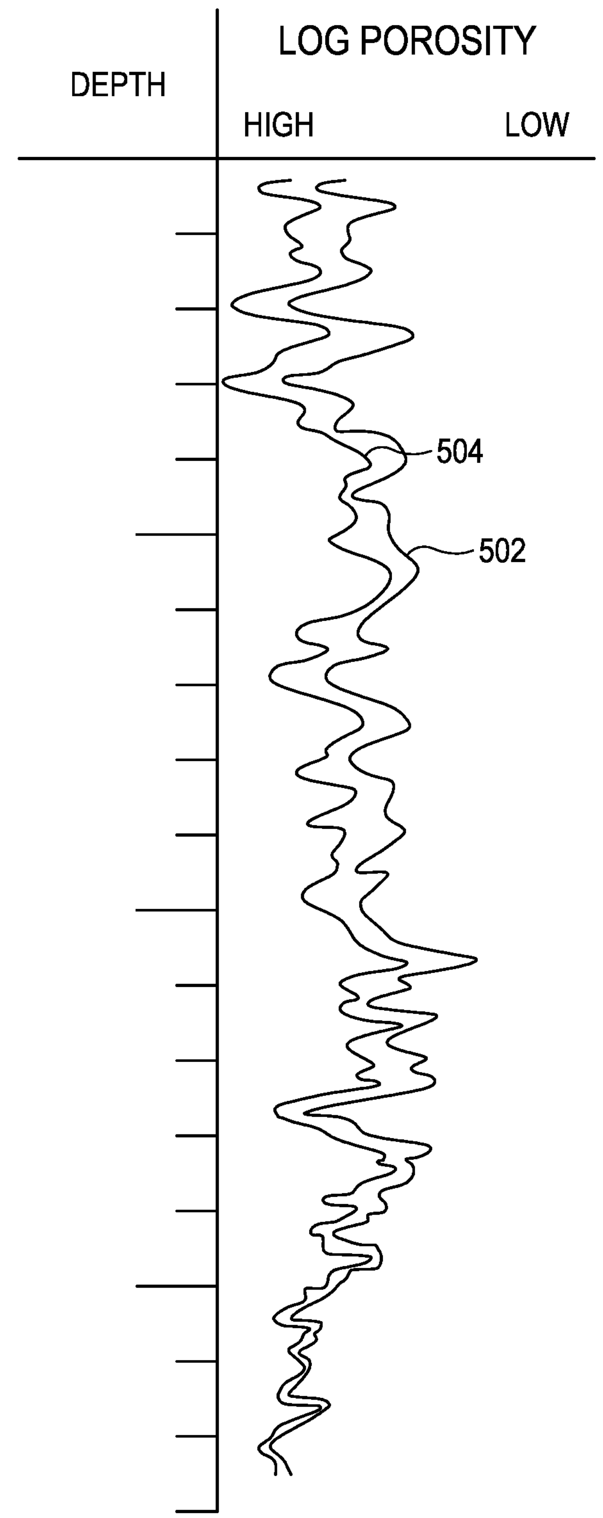
FIG. 5 is an example plot comparing uncorrected and corrected porosity values throughout the depth of a wellbore.

FIG. 5 is an example plot 500 comparing uncorrected and corrected porosity values throughout the depth of a wellbore. The line 502 represents the level of the porosity that has been determined within a rock sample (e.g., the rock sample 100) by the prior art and state of the art processes. Utilizing the methods and systems described herein, the line 504 represents the corrected porosity determined within the same rock sample as an output of the inventive process in the present disclosure. It may be seen in the plot 500 that the difference between the prior art determination of the uncorrected porosity and the corrected porosity of the present disclosure, represented by the space between the line 502 and the line 504, is greater in sections of the reservoir. At different depths, the correction of the porosity may require more adjustments related to the location of the cements and the trendline calculation. Therefore, changes in the porosity are determined, which allow the reservoir management decisions to be properly informed by the information presented in line 504.

The terminology used herein is for the purpose of describing particular embodiments only and is not intended to be limiting of the invention. As used herein, for example, the singular forms "a," "an," and "the" are intended to include the plural forms as well, unless the context clearly indicates otherwise. It will be further understood that the terms "contains", "containing", "includes", "including," "comprises", and/or "comprising," and variations thereof, when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing and are not to be construed as limiting. However, it is recognized these terms could be used with reference to an operator or user. Accordingly, no limitations are implied or to be inferred. In addition, the use of ordinal numbers (e.g., first, second, third, etc.) is for distinction and not counting. For example, the use of "third" does not imply there must be a corresponding "first" or "second." Also, if used herein, the terms "coupled" or "coupled to" or "connected" or "connected to" or "attached" or "attached to" may indicate establishing either a direct or indirect connection, and is not limited to either unless expressly referenced as such.

While the disclosure has described several exemplary embodiments, it will be understood by those skilled in the art that various changes can be made, and equivalents can be substituted for elements thereof, without departing from the spirit and scope of the invention. In addition, many modifications will be appreciated by those skilled in the art to adapt a particular instrument, situation, or material to embodiments of the disclosure without departing from the essential scope thereof. Therefore, it is intended that the invention not be limited to the particular embodiments disclosed, or to the best mode contemplated for carrying out this invention, but that the invention will include all embodiments falling within the scope of the appended claims. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative.

In view of the foregoing structural and functional description, those skilled in the art will appreciate that portions of the embodiments may be embodied as a method, data processing system, or computer program product. Accordingly, these portions of the present embodiments may take the form of an entirely hardware embodiment, an entirely software embodiment, or an embodiment combining software and hardware, such as shown and described with respect to the computer system of FIG. 6. Furthermore, portions of the embodiments may be a computer program product on a computer-usable storage medium having computer readable program code on the medium. Any non-transitory, tangible storage media possessing structure may be utilized including, but not limited to, static and dynamic storage devices, hard disks, optical storage devices, and magnetic storage devices, but excludes any medium that is not eligible for patent protection under 35 U.S.C. § 101 (such as a propagating electrical or electromagnetic signal per se). As an example and not by way of limitation, a computer-readable storage media may include a semiconductor-based circuit or device or other IC (such, as for example, a field-programmable gate array (FPGA) or an ASIC), a hard disk, an HDD, a hybrid hard drive (HHD), an optical disc, an optical disc drive (ODD), a magneto-optical disc, a magneto-optical drive, a floppy disk, a floppy disk drive (FDD), magnetic tape, a holographic storage medium, a solid-state drive (SSD), a RAM-drive, a SECURE DIGITAL card, a SECURE DIGITAL drive, or another suitable computer-readable storage medium or a combination of two or more of these, where appropriate. A computer-readable non-transitory storage medium may be volatile, nonvolatile, or a combination of volatile and non-volatile, where appropriate.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 6:
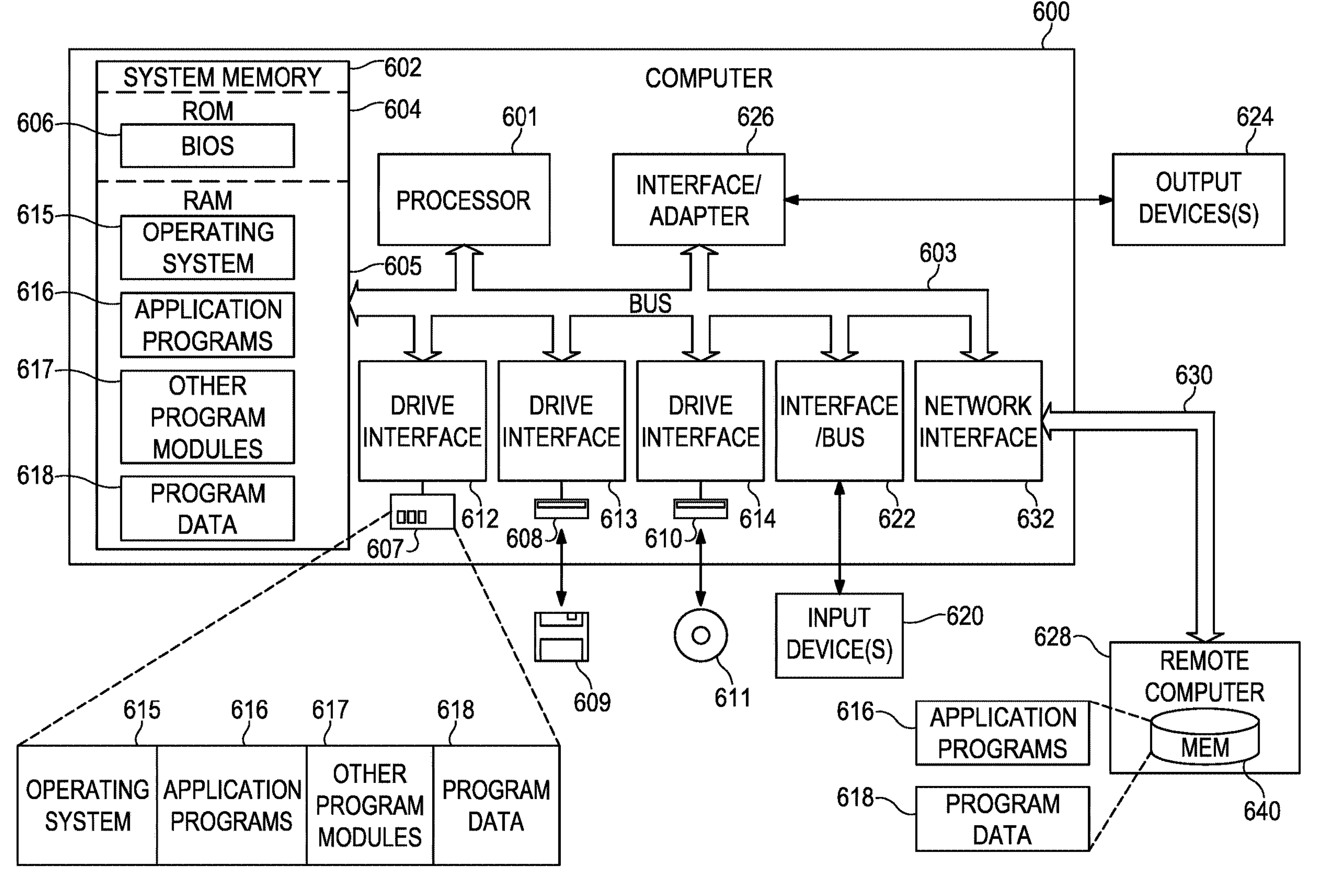
FIG. 6 is an example of a computer system that can be employed to execute one or more embodiments of the present disclosure.

In this regard, FIG. 6 illustrates one example of a computer system 600 that can be employed to execute one or more embodiments of the present disclosure. Computer system 600 can be implemented on one or more general purpose networked computer systems, embedded computer systems, routers, switches, server devices, client devices, various intermediate devices/nodes or standalone computer systems. Additionally, computer system 600 can be implemented on various mobile clients such as, for example, a personal digital assistant (PDA), laptop computer, pager, and the like, provided it includes sufficient processing capabilities.

Computer system 600 includes processing unit 601, system memory 602, and system bus 603 that couples various system components, including the system memory 602, to processing unit 601. Dual microprocessors and other multiprocessor architectures also can be used as processing unit 601. System bus 603 may be any of several types of bus structure including a memory bus or memory controller, a peripheral bus, and a local bus using any of a variety of bus architectures. System memory 602 includes read only memory (ROM) 604 and random access memory (RAM) 605. A basic input/output system (BIOS) 606 can reside in ROM 604 containing the basic routines that help to transfer information among elements within computer system 600.

Computer system 600 can include a hard disk drive 607, magnetic disk drive 608, e.g., to read from or write to removable disk 609, and an optical disk drive 610, e.g., for reading CD-ROM disk 611 or to read from or write to other optical media. Hard disk drive 607, magnetic disk drive 608, and optical disk drive 610 are connected to system bus 603 by a hard disk drive interface 612, a magnetic disk drive interface 613, and an optical drive interface 614, respectively. The drives and associated computer-readable media provide nonvolatile storage of data, data structures, and computer-executable instructions for computer system 600. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of embodiments shown and described herein.

A number of program modules may be stored in drives and ROM 604, including operating system 615, one or more application programs 616, other program modules 617, and program data 618. The application programs 616 and program data 618 can include functions and methods programmed to generate a computer-aided tomography index (e.g., at 411), generate a trendline from compiled data (e.g., at 423), calculate corrected petrophysical properties (e.g., at 441), and utilize the corrected petrophysical properties in reservoir management, as well as other functions and methods shown and described herein.

A user may enter commands and information into computer system 600 through one or more input devices 620, such as a pointing device (e.g., a mouse, touch screen), keyboard, microphone, joystick, game pad, scanner, and the like. These and other input devices 620 are often connected to processing unit 601 through a corresponding port interface 622 that is coupled to the system bus, but may be connected by other interfaces, such as a parallel port, serial port, or universal serial bus (USB). One or more output devices 624 (e.g., display, a monitor, printer, projector, or other type of displaying device) is also connected to system bus 603 via interface 626, such as a video adapter.

Computer system 600 may operate in a networked environment using logical connections to one or more remote computers, such as remote computer 628. Remote computer 628 may be a workstation, computer system, router, peer device, or other common network node, and typically includes many or all the elements described relative to computer system 600. The logical connections, schematically indicated at 630, can include a local area network (LAN) and a wide area network (WAN). When used in a LAN networking environment, computer system 600 can be connected to the local network through a network interface or adapter 632. When used in a WAN networking environment, computer system 600 can include a modem, or can be connected to a communications server on the LAN. The modem, which may be internal or external, can be connected to system bus 603 via an appropriate port interface. In a networked environment, application programs 616 or program data 618 depicted relative to computer system 600, or portions thereof, may be stored in a remote memory storage device 640.

The invention claimed is:

1. A method for characterizing an oil/gas, or water well comprising:

recovering a core sample from a borehole of the oil/gas or water well;

performing a computer-aided tomography scan on the core sample;

obtaining measurements of petrophysical properties relating to the oil/gas or water well;

deriving a computer-aided tomography index from the computer-aided tomography scan;

correcting the measurements of petrophysical properties as a function of the computer-aided tomography index;

obtaining cement phase elemental concentration values from the subterranean formation via borehole geochemical logging tools;

generating a trendline that correlates the cement phase element concentration values with the computer-aided tomography index;

receiving cement phase elemental concentration data for a further oil/gas or water well without an available core sample via the borehole geochemical logging tools;

predicting, via the trendline, a computer-aided tomography index from the cement phase element concentration data for the further oil/gas or water well;

developing a model of a subterranean formation using the measurements that were corrected; and performing reservoir management activities within the subterranean formation using the model of the subterranean formation, wherein the measurements of petrophysical properties that are corrected comprise grain density, porosity, permeability, storage capacity, or any combination thereof, and wherein the reservoir management activities comprise altering reservoir models, adjusting estimated reservoir volume, adjusting projected flowrate, optimizing wellbore design, altering a depletion plan, preemptively correcting reservoir issues within the subterranean formation, or any combination thereof.

2. The method of claim 1, wherein the borehole geochemical logging tools comprise an elemental capture spectroscopy device, a pulsed neutron spectroscopy device, and any combination thereof.

3. The method of claim 1, wherein performing reservoir management activities within the subterranean formation uses the measurements of petrophysical properties in combination with the model of the subterranean formation.

4. The method of claim 1, further comprising receiving reservoir fluid data measured within the subterranean formation, wherein the reservoir fluid data is used in correcting the measurements of petrophysical properties.

5. A system comprising:

a scanner operable to perform a computer-aided tomography scan of a recovered core sample from a subterranean formation;

a geochemical logging tool operable to obtain cement phase elemental concentrations within the subterranean formation; and an electronic device in communication with the scanner, the electronic device comprising:

a processor; and a non-transitory computer-readable medium storing machine-readable instructions, which, when executed by the processor, cause the electronic device to:

receive the computer-aided tomography scan;

generate a computer-aided tomography index of the core sample using the computer-aided tomography scan;

calculate corrected petrophysical properties for the subterranean formation and an associated reservoir from the computer-aided tomography index;

generate a trendline which correlates historical cement phase element concentration data with computer-aided tomography index data including the computer aided tomography index of the core sample;

obtain cement phase elemental concentration data for a further oil/gas or water well without an available core sample via the geochemical logging tool;

predict, via the trendline, a computer-aided tomography index from the cement phase element concentration data for the further oil/gas or water well; and perform reservoir management utilizing the corrected petrophysical properties, wherein the measurements of petrophysical properties that are corrected comprise grain density, porosity, permeability, storage capacity, or any combination thereof, and wherein the reservoir management performed is an element selected from a group consisting of alteration of reservoir models, adjustment of estimated reservoir volume, adjustment of projected flowrate, optimization of wellbore design, alteration of a depletion plan, a preemptive correction of reservoir issues, and any combination thereof.

6. The system of claim 5, wherein the machine-readable instructions further cause the electronic device to: receive reservoir fluid data from downhole samples, wherein the reservoir fluid data is used to calculate the corrected petrophysical properties for the subterranean formation and the associated reservoir.

7. The system of claim 5, further comprising a database storing the historical values of the computer-aided tomography index and cement phase elemental concentrations.

8. The system of claim 7, wherein the machine-readable instructions further cause the electronic device to: add the additional cement phase element concentration and the computer-aided tomography index to the database.

9. The system of claim 5, wherein the computer-aided tomography index is generated based upon a porosity of the core sample, a ratio of diagenetic phases with higher or lower density cements present within the core sample, a representative grain density value, or any combination thereof.

10. A method for characterizing an oil/gas, or water well comprising:

recovering a core sample from a borehole of the oil/gas or water well;

performing a computer-aided tomography scan on the core sample;

obtaining measurements of petrophysical properties relating to the oil/gas or water well;

deriving a computer-aided tomography index from the computer-aided tomography scan;

correcting the measurements of petrophysical properties as a function of the computer-aided tomography index;

generating a trendline that correlates historical cement phase element concentration data with computer-aided tomography index data;

obtaining cement phase elemental concentration data for a further oil/gas or water well without an available core sample via a geochemical logging tool;

predicting, via the trendline, a computer-aided tomography index from the cement phase element concentration data for the further oil/gas or water well;

developing a model of a subterranean formation using the measurements that were corrected; and performing reservoir management activities within the subterranean formation using the model of the subterranean formation, wherein the measurements of petrophysical properties that are corrected comprise grain density, porosity, permeability, storage capacity, or any combination thereof, and wherein the reservoir management activities comprise altering reservoir models, adjusting estimated reservoir volume, adjusting projected flowrate, optimizing wellbore design, altering a depletion plan, preemptively correcting reservoir issues within the subterranean formation, or any combination thereof.

11. The method of claim 10, further comprising: predicting, via the trendline, a cement phase element concentration from a computer-aided tomography index derived from a computer-aided tomography scan.

12. The method of claim 10, wherein the computer-aided tomography index is derived based upon a ratio of diagenetic phases with higher or lower density cements present within the core sample, a representative grain density value, or a combination thereof.

13. The method of claim 10, wherein the core sample includes a patchy cement phase distribution in a rock matrix.

* * * * *